US009032606B2

(12) United States Patent  
Horkey (10) Patent No.: US 9,032,606 B2
(45) Date of Patent: May 19, 2015

(54) SYSTEMS AND METHODS FOR PERSONALIZING PROSTHETIC AND ORTHOTIC DEVICES

(76) Inventor: Dan Horkey, Port Orchard, WA (US)

( * ) Notice: Subject to any disclaimer, the term of this patent is extended or adjusted under 35 U.S.C. 154(b) by 424 days.

(21) Appl. No.: 12/898,563

(22) Filed: Oct. 5, 2010

(65) Prior Publication Data

US 2011/0078888 A1    Apr. 7, 2011

Related U.S. Application Data

(60) Provisional application No. 61/248,856, filed on Oct. 5, 2009.

(51) Int. Cl.
  B23P 11/02    (2006.01)
  A61F 2/50    (2006.01)
  A61F 5/01    (2006.01)

(52) U.S. Cl.
  CPC .............. *A61F 2/50* (2013.01); *A61F 2/5044* (2013.01); *A61F 2/5046* (2013.01); *A61F 5/01* (2013.01); *A61F 2002/5001* (2013.01)

(58) Field of Classification Search
  CPC ............ A61F 2/50; A61F 5/01; A61F 2/5046
  USPC ............. 29/428, 458, 600, 832, 854, 447, 55;
      399/265, 329; 358/3.17, 3.18, 3.29;
      623/33–36, 901; 700/92–98; 703/1
  See application file for complete search history.

(56) References Cited

U.S. PATENT DOCUMENTS

| 1,999,413 | A | * | 4/1935 | Hemming et al. | 156/237 |
|---|---|---|---|---|---|
| 2,294,479 | A | * | 9/1942 | Peter | 427/335 |
| 4,225,369 | A | * | 9/1980 | Felchlin | 156/71 |
| 4,268,922 | A | * | 5/1981 | Marsh et al. | 623/38 |
| 5,026,392 | A | * | 6/1991 | Gordon | 623/6.64 |
| 5,088,484 | A | * | 2/1992 | Freeman et al. | 602/44 |
| 5,525,290 | A | * | 6/1996 | Carpenter | 264/510 |
| 5,573,501 | A | * | 11/1996 | Ruscito et al. | 602/7 |
| 5,782,638 | A | * | 7/1998 | Warren et al. | 433/206 |
| 5,856,267 | A | * | 1/1999 | Sherman et al. | 503/227 |
| 5,994,264 | A | * | 11/1999 | Sherman et al. | 503/227 |
| 6,015,469 | A | * | 1/2000 | Fenzi | 156/230 |
| 6,387,474 | B1 | * | 5/2002 | Richards | 428/204 |
| D489,491 | S | * | 5/2004 | Corser | D29/106 |
| D507,653 | S | * | 7/2005 | Batchelor | D24/190 |
| 7,101,604 | B1 | * | 9/2006 | Minges | 428/141 |
| 7,260,882 | B2 | * | 8/2007 | Credelle et al. | 29/600 |
| 7,402,223 | B2 | * | 7/2008 | Marks et al. | 156/247 |
| 2008/0156885 | A1 | * | 7/2008 | Landau et al. | 235/492 |
| 2009/0090002 | A1 | * | 4/2009 | Motomuro | 29/832 |
| 2012/0226197 | A1 | * | 9/2012 | Sanders et al. | 600/587 |
| 2012/0252329 | A1 | * | 10/2012 | Wald et al. | 451/527 |

* cited by examiner

*Primary Examiner* — Minh Trinh (57) ABSTRACT

Systems and methods for personalizing prosthetic and orthotic devices are disclosed. In some embodiments, a method of personalizing a portion of a device configured to be worn by a wearer as at least one of a prosthetic or an orthosis may include facilitating an application of a wearer-selected artwork to the portion of the device. For example, in various specific embodiments, the facilitating an application of a wearer-selected artwork to the portion of the device may include creating a portion of material having a wearer-specified personalization artwork, and providing the portion of material having the wearer-specified personalization artwork to at least one of the wearer or a third party for application onto the portion of the device. In some embodiments, the portion of material may be provided to at least one of the wearer or a third party for application when the portion of the device is being fabricated.

19 Claims, 11 Drawing Sheets

SYSTEMS AND METHODS FOR PERSONALIZING PROSTHETIC AND ORTHOTIC DEVICES

CROSS REFERENCE TO RELATED APPLICATIONS

This patent application claims benefits under 35 USC §119 (e) from the following provisional patent application: U.S. Patent Application No. 61/248,856 filed on Oct. 5, 2009, which application is incorporated herein by reference.

FIELD OF THE INVENTION

The present disclosure is directed to systems and methods for personalizing prosthetic and orthotic devices.

BACKGROUND OF THE INVENTION

A person's loss of a limb can be a potentially devastating event. Recovery can be a long and arduous process involving physical and psychological adjustment. Although conventional approaches to personalizing prosthetic and orthotic devices have achieved desirable results, there is room for improvement.

SUMMARY

The present disclosure teaches systems and methods for personalizing prosthetic and orthotic devices. Embodiments of systems and methods in accordance with the teachings of the present disclosure may advantageously improve a wearer's satisfaction and comfort with a device configured to be worn as a prosthetic or orthotic component.

For example, in one embodiment, a method of personalizing a portion of a device comprises: cleaning the portion of the device; dry-sanding the portion of the device; coating the portion of the device with a primer; wet-sanding the portion of the device; base-coating the portion of the device with a basecoat; applying one or more substantially-clear coatings to the portion of the device; applying one or more intermediate coatings to the portion of the device (optional); wet-sanding the one or more intermediate coatings; applying a wearer-selected artwork to the portion of the device; and applying one or more substantially-clear coatings over the wearer-selected artwork. In specific embodiments, for example, applying a wearer-selected artwork to the portion of the device may comprise applying a camera photo provided by the wearer to the portion of the device, applying a portrait photo provided by the wearer to the portion of the device, or applying at least one of a clip art or a graphic provided by the wearer to the portion of the device.

In another embodiment, a method of personalizing a portion of a device configured to be worn by a wearer as at least one of a prosthetic or an orthosis may include facilitating an application of a wearer-selected artwork to the portion of the device. For example, in specific embodiments, the facilitating an application of a wearer-selected artwork to the portion of the device may include creating a portion of material having a wearer-specified personalization artwork, and providing the portion of material having the wearer-specified personalization artwork to at least one of the wearer or a third party for application onto the portion of the device. More specifically, the portion of material may be provided to at least one of the wearer or a third party for application when the portion of the device is being fabricated.

Other embodiments and advantages that may be provided by systems and methods in accordance with the present disclosure will become apparent during review of the following disclosure.

BRIEF DESCRIPTION OF THE DRAWINGS

Embodiments of the present disclosure are described in detail below with reference to the following drawings.

DETAILED DESCRIPTION

The present disclosure is directed to systems and methods for personalizing prosthetic and orthotic devices. Many specific details of certain embodiments in accordance with the present disclosure are set forth in the following description and in FIGS. 1-27 to provide a thorough understanding of such embodiments. One skilled in the art, however, will understand that the present invention may have additional embodiments, or that the invention may be practiced without several of the details described in the following description.

Figure 1:
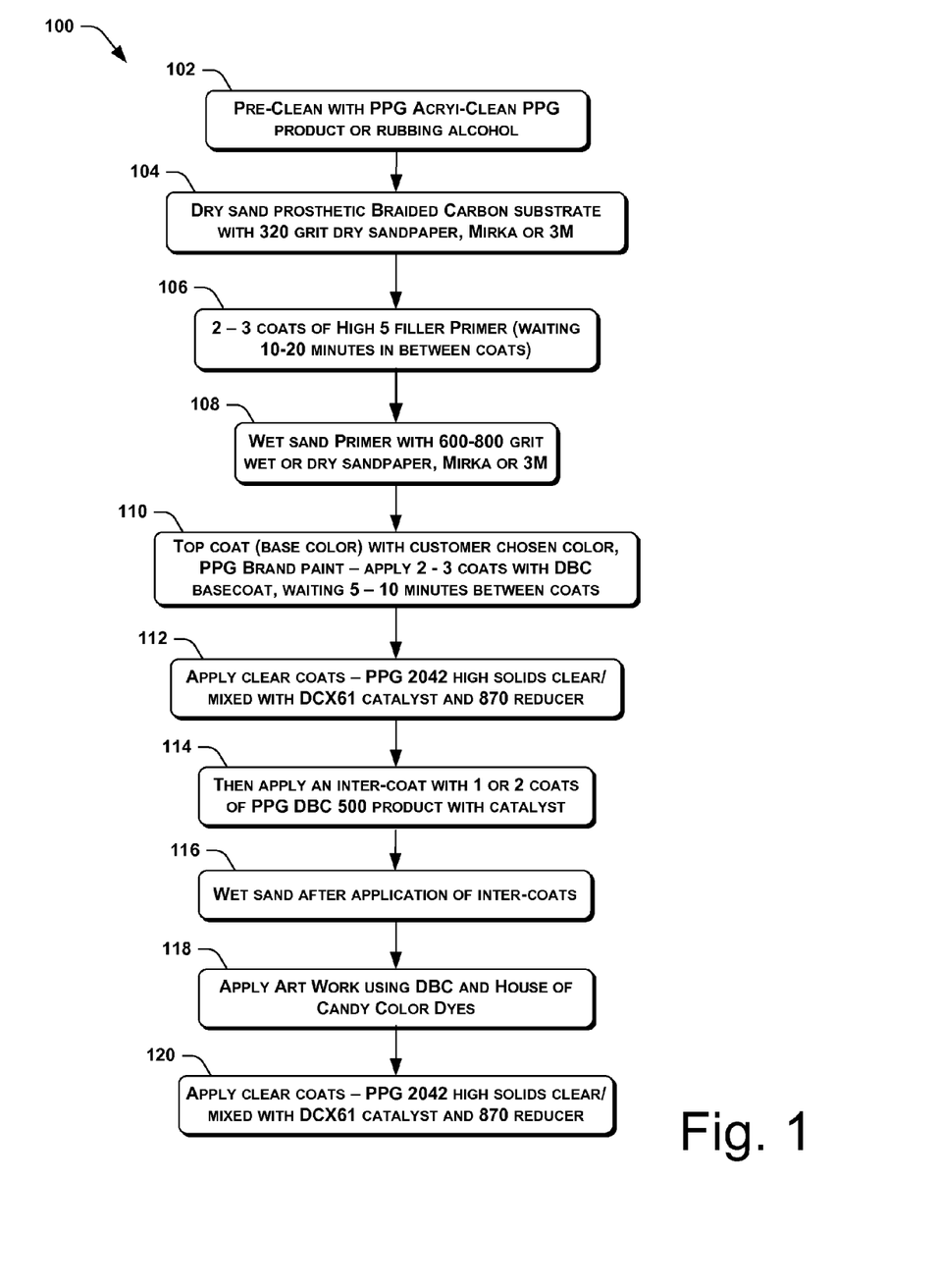
FIG. 1 is a flowchart showing a method of personalizing prosthetic or orthotic devices in accordance with an embodiment of the present disclosure.

FIG. 1 is a flowchart showing a method 100 of personalizing prosthetic or orthotic devices in accordance with an embodiment of the present disclosure. More specifically, in at least some embodiments, the method 100 may include painting carbon braid, nylon, co-poly, poly-pro, and/or other common trade specific plastics used as substrates for prosthetic sockets and orthosis (a.k.a. orthotic braces), however, in alternate embodiments, other types and compositions of prosthetic and orthosis may be personalized. As shown in FIG. 1, in this embodiment, the method 100 includes:

(a) Pre-Clean with PPG Acryi-Clean PPG product or rubbing alcohol (at 102);

(b) Dry sand prosthetic Braided Carbon substrate with 320 grit dry sandpaper, Mirka or 3M (at 104);

(c) 2-3 coats of High 5 filler Primer (waiting 10-20 minutes in between coats) (at 106) Note: Braided carbon substrate would also accept a Primer base coat PPG K-36 product;

(d) Wet sand Primer with 600-800 grit wet or dry sandpaper, Mirka or 3M (at 108)

(e) Base coat (base color) with customer chosen color, PPG Brand paint—apply 2-3 coats with DBC basecoat, waiting 5-10 minutes between coats (at 110)

(f) Apply clear coats—PPG 2042 high solids clear/mixed with DCX61 catalyst and 870 reducer (at 112);

(g) Optional step: then apply an inter-coat with 1 or 2 coats of PPG DBC 500 product with catalyst (at 114); in at least some embodiments, DCB is an additional prep hardener with catalyst that may need to be applied over the previous coat of 2042; Basically, a form of prep prior to airbrushing artwork;

(h) Wet sand after application of inter-coats (at 116);

(i) Apply Art Work using DBC and/or House of Candy Color Dyes (at 118); the applying at 118 may include airbrushing and/or hand-painting; and (j) Apply clear coats—PPG 2042 high solids clear/mixed with DCX61 catalyst and 870 reducer (at 120).

As noted above, the applying of personalizing artwork at 118 may include airbrushing and/or hand-painting. No conventional methods of personalizing prosthetic or orthotic devices are known that include airbrushing and/or hand-painting as disclosed herein. In addition, in some embodiments, methods in accordance with the teachings of the present disclosure may use one or more of automotive dyes, paints, or concentrated colored pigments which may be mixed into an acrylic resin and installed during fabrication, and can be used on orthotic and prosthetic devices (e.g. devices shown in FIGS. 2-10).

Embodiments of methods in accordance with the present disclosure may advantageously provide an option to a "wearer" for an opportunity to personalize a prosthetic socket or orthotic "orthosis" brace that is otherwise not available in the market. For example, in some embodiments, a wearer may provide their individual choice of personalization artwork (e.g. clip art, graphics, personal camera photos and portrait photos in JPEG, PNG, GIF, TIF etc.) for application onto a device, thus allowing a wearer to choose their own custom "tattoo" or personalization.

More specifically, in some embodiments, a file containing personalization artwork provided by a wearer may be modified (e.g. using Photoshop or other suitable software) to create a collage or other specified design full prints by means of, for example, "sublimation printing" (or other suitable sub-process) on a material (e.g. polyester or cotton fabric for prosthetics and transfer paper custom paper prints to be applied on various plastic types as shown in FIG. 2 thru FIG. 10). A particular size of the material may vary depending on the particular device (e.g. prosthetic, brace, etc.) being personalized (typically sizes ranging in 12" sq. up to 36"sq. have been found to be suitable). In some embodiments, the resulting custom "tattoo" fabric and/or paper prints may be shipped to the wearer or prosthetist to apply when a new device is being fabricated.

It will be appreciated that one or more of the above-referenced actions of the method 100 may be optional (even if not expressly stated above) and may be omitted without departing from the spirit and scope of the invention.

Figure 2:
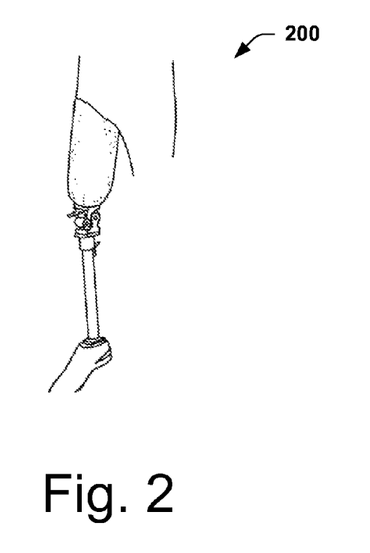
FIG. 2 is a front isometric view of an exemplary above-knee prosthetic device in accordance with an embodiment of the present disclosure.

FIG. 2 is a front isometric view of an exemplary above-knee prosthetic device 200 in accordance with an embodiment of the present disclosure.

Figure 3:
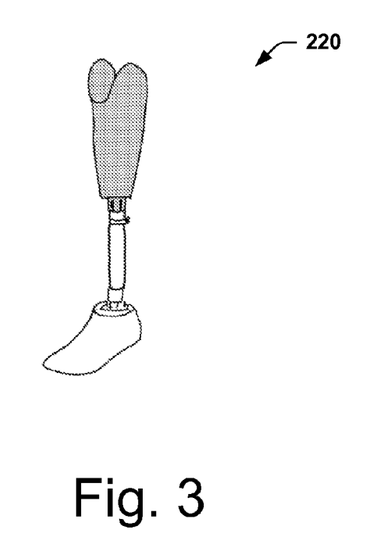
FIG. 3 is a front isometric view of an exemplary below-knee prosthetic device in accordance with an embodiment of the present disclosure.

FIG. 3 is a front isometric view of an exemplary below-knee prosthetic device 220 in accordance with an embodiment of the present disclosure.

Figure 4:
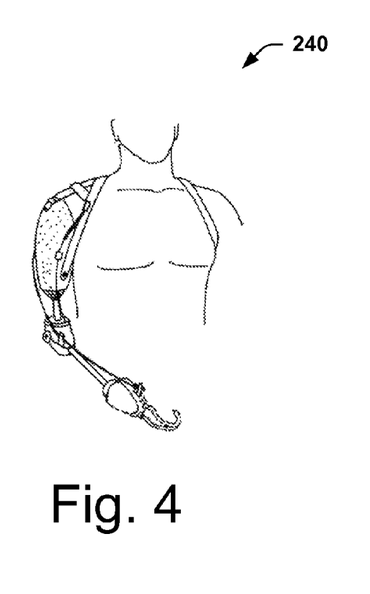
FIG. 4 is a front isometric view of an exemplary upper-extremity prosthetic device in accordance with an embodiment of the present disclosure.

FIG. 4 is a front isometric view of an exemplary upper-extremity prosthetic device 240 in accordance with an embodiment of the present disclosure.

Figure 5:
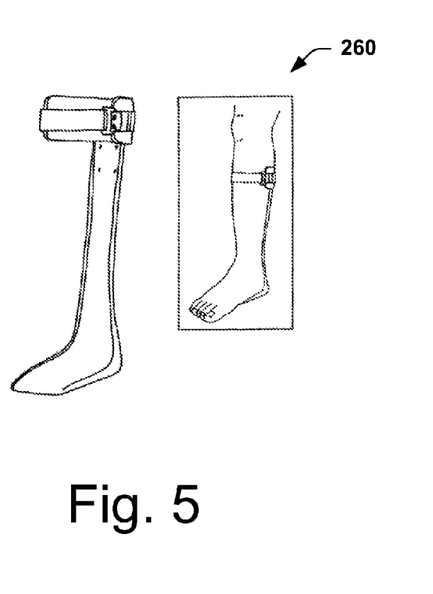
FIGS. 5-10 show front isometric views of exemplary orthotic braces in accordance with alternate embodiments of the present disclosure.

FIG. 5 shows a front isometric view(s) of an exemplary orthotic brace 260 in accordance with an embodiment of the present disclosure.

Figure 6:
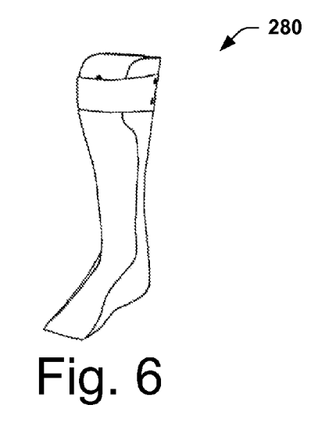

FIG. 6 shows a front isometric view of another exemplary orthotic brace 280 in accordance with an embodiment of the present disclosure.

Figure 7:
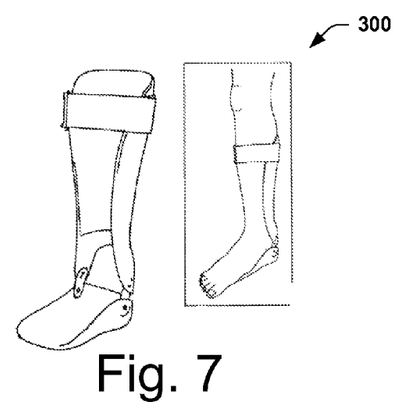

FIG. 7 shows a front isometric view(s) of yet another exemplary orthotic brace 300 in accordance with an embodiment of the present disclosure.

Figure 8:
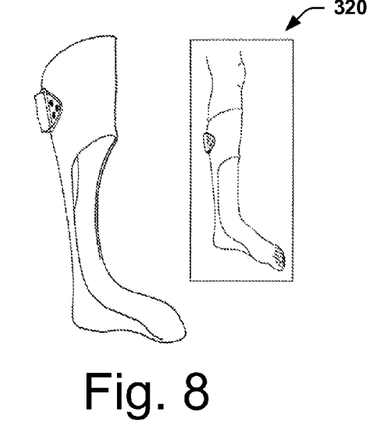

FIG. 8 shows a front isometric view(s) of yet another exemplary orthotic brace 320 in accordance with an embodiment of the present disclosure.

Figure 9:
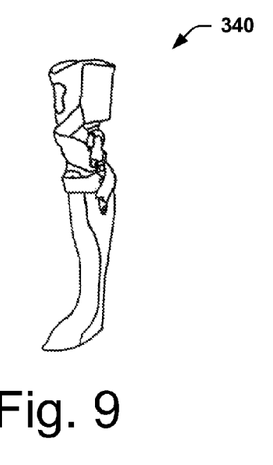

FIG. 9 shows a front isometric view of another exemplary orthotic brace 340 in accordance with an embodiment of the present disclosure.

Figure 10:
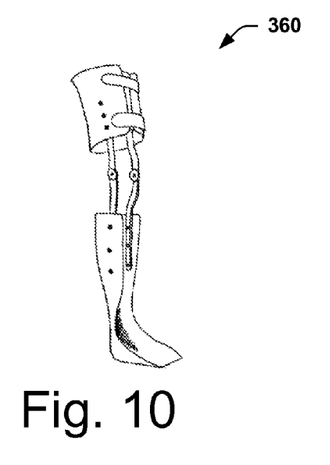

FIG. 10 shows a front isometric view of still another exemplary orthotic brace 360 in accordance with an embodiment of the present disclosure.

Figure 11:
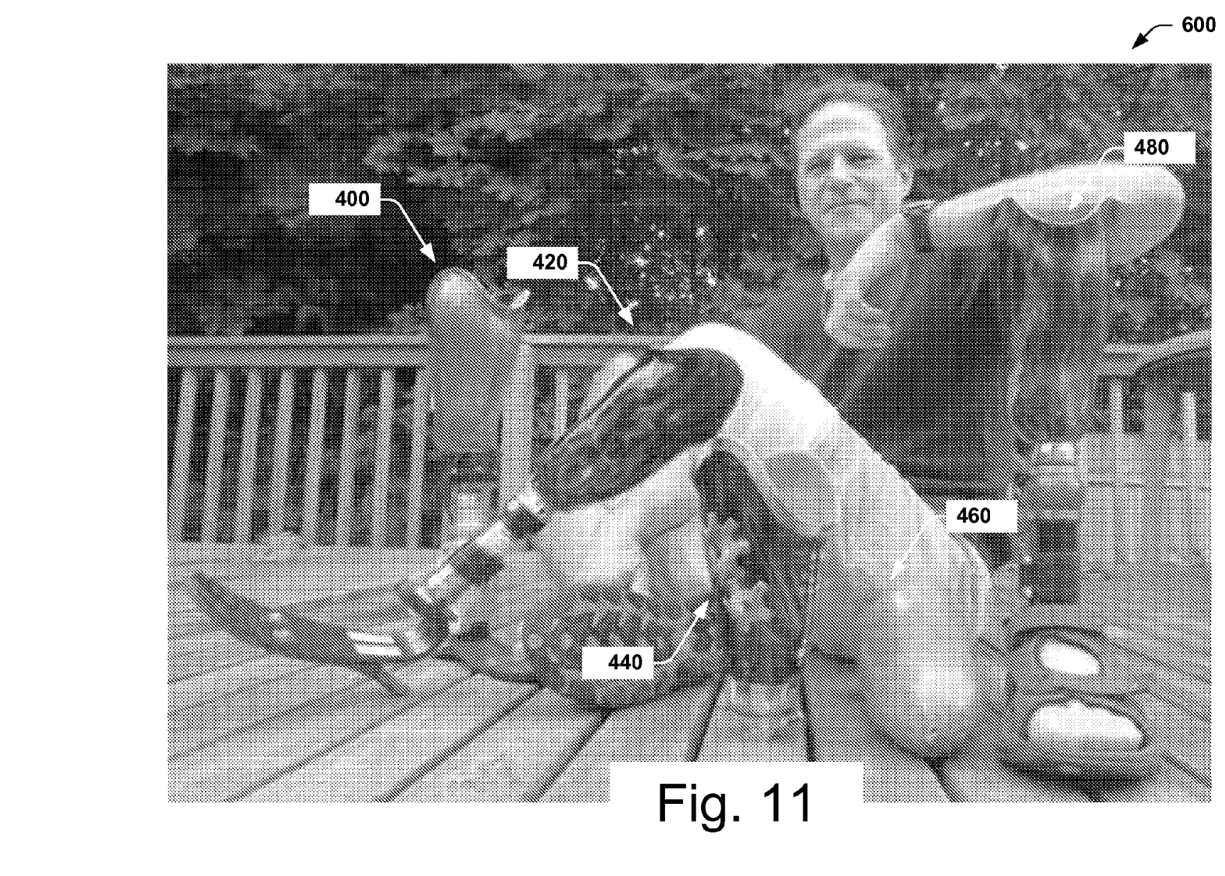
FIGS. 11-27 show isometric views of exemplary personalizations and designs of prosthetic or orthotic devices in accordance with alternate embodiments of the present disclosure.

FIG. 11 shows isometric views of various exemplary personalizations and/or designs of prosthetic or orthotic devices in accordance with alternate embodiments of the present disclosure. More specifically, FIG. 11 shows an embodiment of a first (or "waves") personalization 400, an embodiment of a second (or "real flames") personalization 420, an embodiment of a third (or "termi-nator or bio-mechanical design with gears") personalization 440, an embodiment of a fourth (or "sky") personalization 460, and an embodiment of a fifth (or "fiery flames") custom fabric tattoo personalization 480. In the embodiments shown in FIG. 11, personalizations 420 and 440 are examples of personalizations that have been performed by methods that include one or more of airbrushing and hand-painting.

Figure 12:
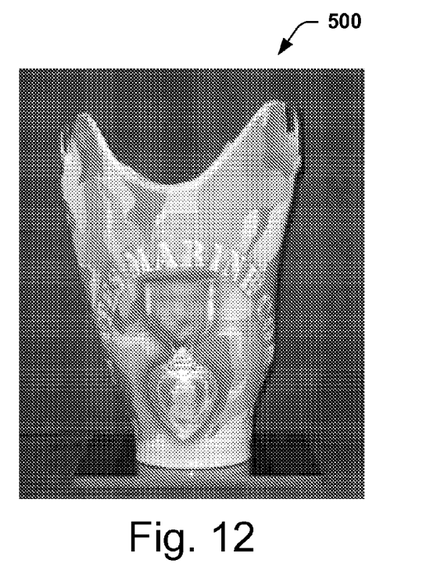

FIG. 12 shows an isometric view of another exemplary personalization and/or design of a prosthetic or orthotic device in accordance with an embodiment of the present disclosure. More specifically, FIG. 12 shows an embodiment of a "purple heart" personalization 500.

Figure 13:
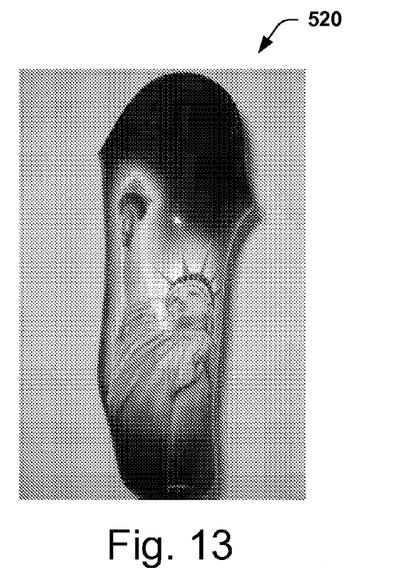

FIG. 13 shows an isometric view of another exemplary personalization and/or design of a prosthetic or orthotic device in accordance with another embodiment of the present disclosure. More specifically, FIG. 13 shows an embodiment of a "liberty" personalization 520.

Figure 14:
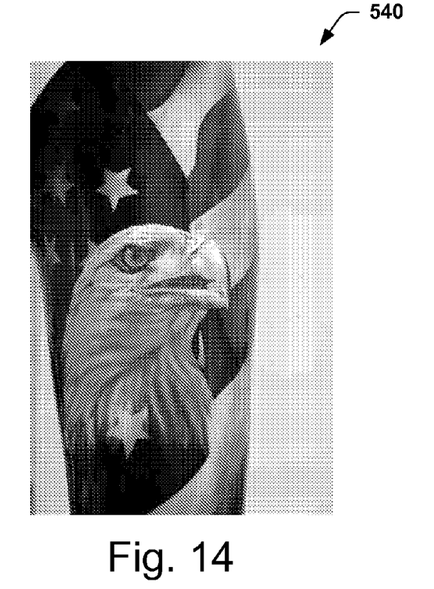

FIG. 14 shows an isometric view of yet another exemplary personalization and/or design of a prosthetic or orthotic device in accordance with another embodiment of the present disclosure. More specifically, FIG. 14 shows an embodiment of an "eagle and flag" personalization 540.

Figure 15:
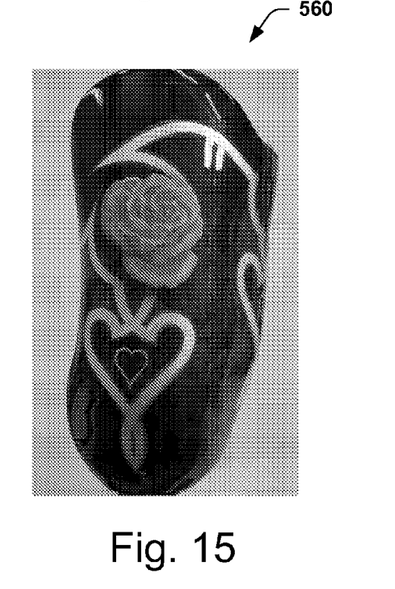

FIG. 15 shows an isometric view of another exemplary personalization and/or design of a prosthetic or orthotic device in accordance with another embodiment of the present disclosure. More specifically, FIG. 15 shows an embodiment of a "rose and heart" personalization 560.

Figure 16:
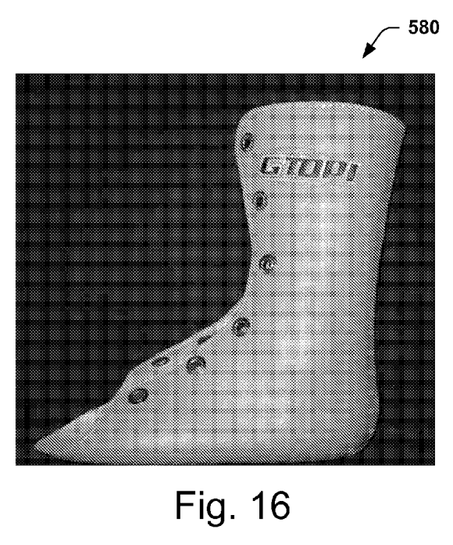

FIG. 16 shows an isometric view of another exemplary personalization and/or design of a prosthetic or orthotic device in accordance with another embodiment of the present disclosure. More specifically, FIG. 16 shows an embodiment of a leather Arizona Brace Ankle-Foot-Orthosis a.k.a AFO with (or without) poly-propelyne, copoly or polypro plastic interface with "embroidery of GTOPI logo" personalization 580.

Figure 17:
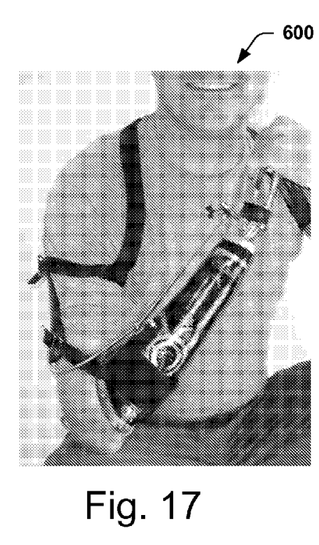

FIG. 17 shows an isometric view of another exemplary personalization and/or design of a prosthetic or orthotic device in accordance with another embodiment of the present disclosure. More specifically, FIG. 17 shows an embodiment of a "mechanical" personalization 600.

Figure 18:
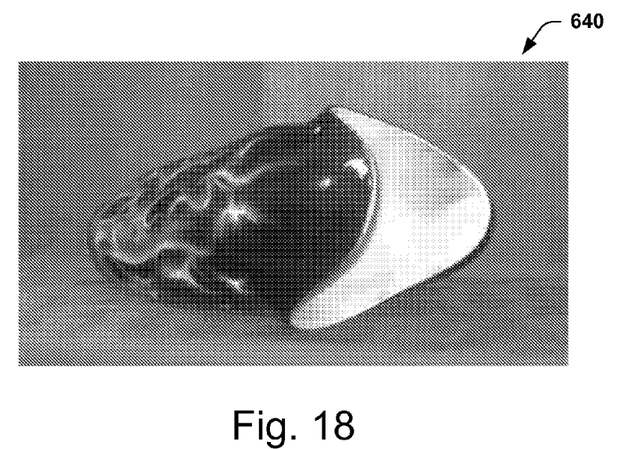

FIG. 18 shows an isometric view of another exemplary personalization and/or design of a prosthetic or orthotic device in accordance with a further embodiment of the present disclosure. More specifically, FIG. 18 shows an embodiment of the first protocol "real flames" personalization 640.

Figure 19:
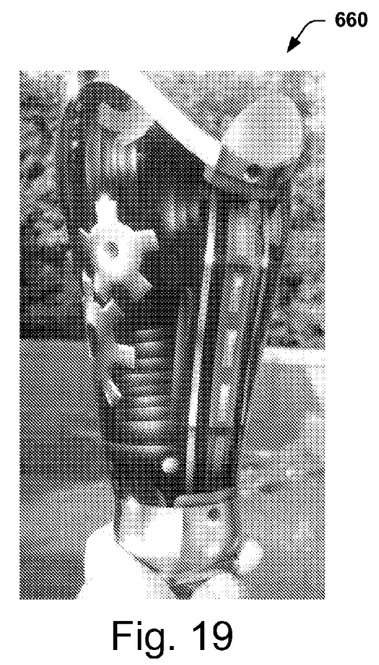

FIG. 19 shows an isometric view of another exemplary personalization and/or design of a prosthetic or orthotic device in accordance with an embodiment of the present disclosure. More specifically, FIG. 19 shows an embodiment of the second protocol "termi-nator or bio-mechanical design with gears" personalization 660.

Figure 20:
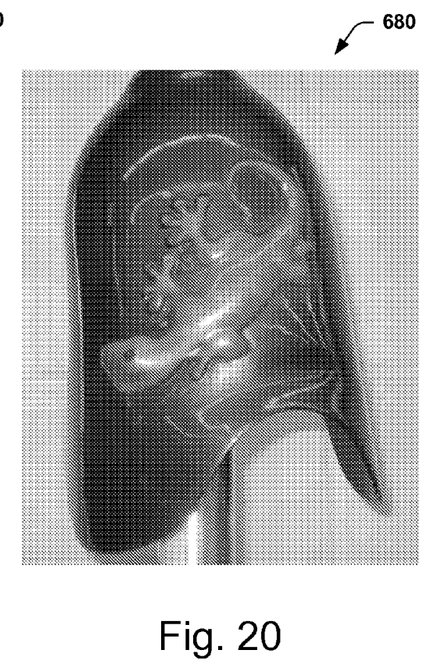

FIG. 20 shows an isometric view of another exemplary personalization and/or design of a prosthetic or orthotic device in accordance with another embodiment of the present disclosure. More specifically, FIG. 20 shows an embodiment of a first type of "3D fiberglass mold of gecko" personalization 680. In at least some embodiments, the "3D fiberglass mold of gecko" personalization 680 involves applying a molded or shaped three-dimensional (3D) piece of artwork that is secured onto the prosthetic or orthotic device. For example, in some embodiments, the 3D piece of artwork is epoxied and placed onto the substrate (whether it be carbon braid or painted surface). Of course, other suitable methods of securing the 3D piece of artwork may be used.

Figure 21:
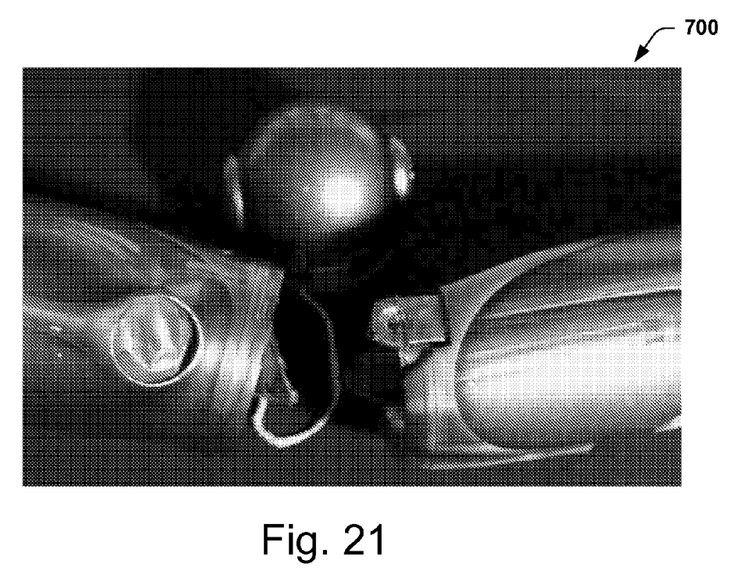
Figure 22:
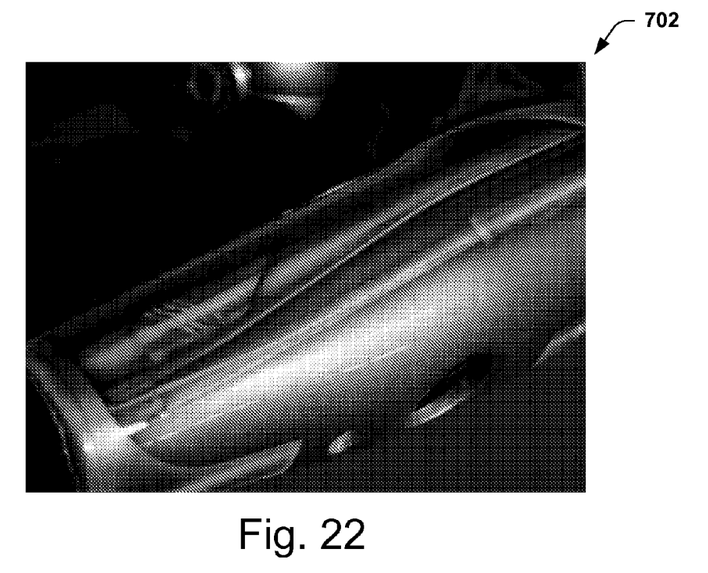
Figure 23:
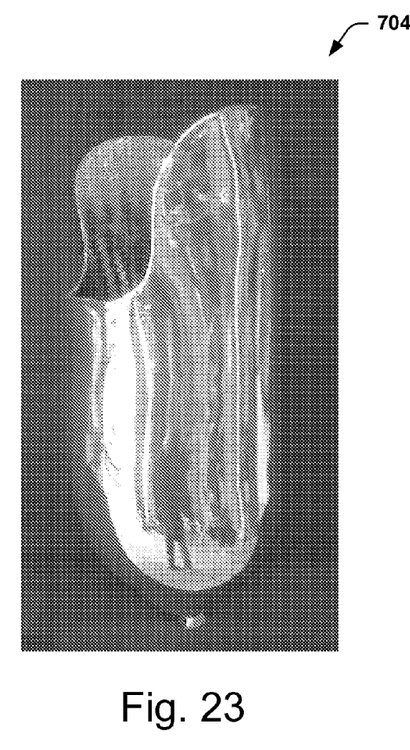
Figure 24:
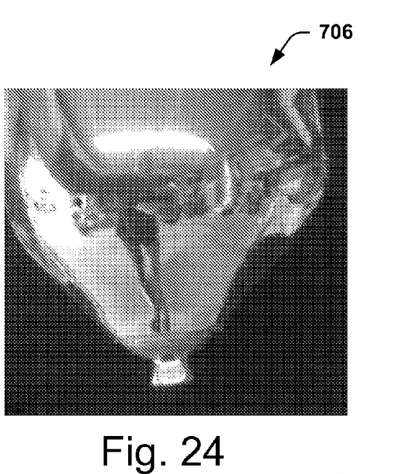
Figure 25:
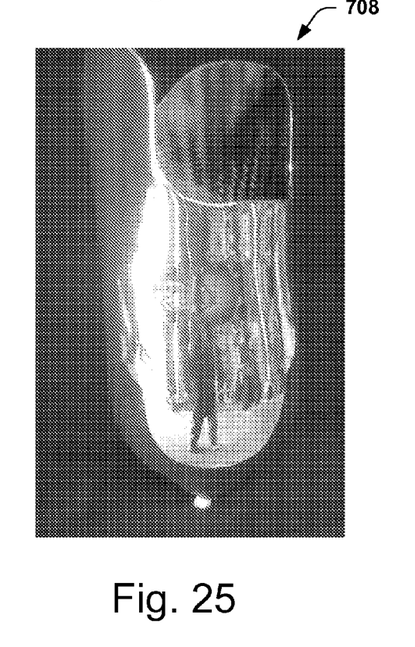

FIGS. 21-25 show alternate isometric views of another exemplary personalization and/or design of a prosthetic or orthotic device in accordance with another embodiment of the present disclosure. More specifically, FIG. 21 shows an embodiment of a "chrome background" personalization 700. FIG. 22 shows an enlarged partial view 702 of the "chrome background" personalization 700 of FIG. 21. FIGS. 23-25 show additional isometric views of a "chrome background" personalization 704, 706, 708. In at least some embodiments, performing a "chrome background" personalization may include procedures substantially similar to prep and paint processes described herein, and may use materials to provide an appearance of one or more of chrome, brass, gold, silver and other metals. More specifically, in some embodiments, performing a "chrome background" personalization may include procedures currently available from SpectraChrome™ or Cosmichrome™.

Figure 26:
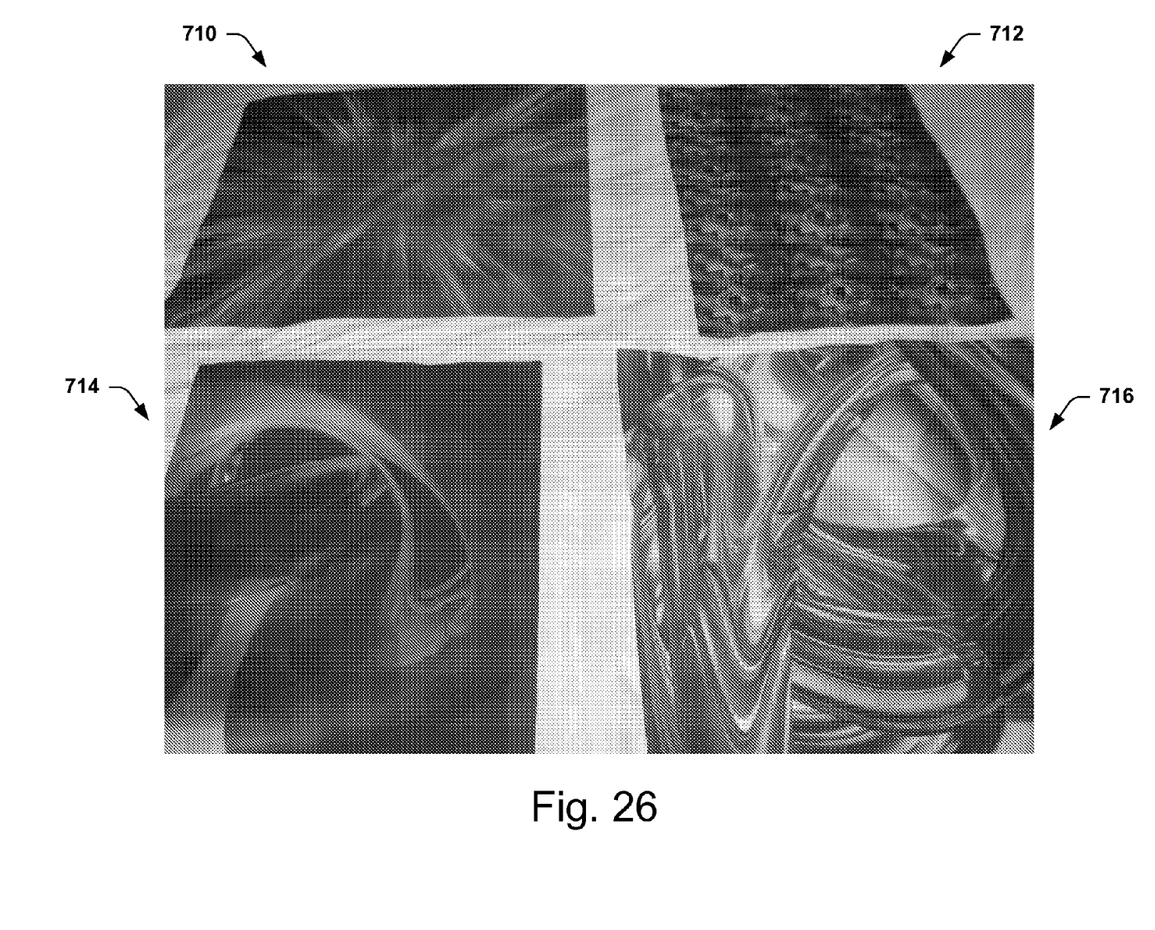

FIG. 26 shows isometric views of various exemplary personalizations and/or designs for application to prosthetic or orthotic devices in accordance with further embodiments of the present disclosure. More specifically, FIG. 26 shows portions of material personalized for application on a device by a wearer or third party (e.g. subsequent to or during fabrication). In specific embodiments, the personalized material portions shown in FIG. 26 may be referred to as custom tattoo fabric and/or transfer paper, and may be applied to orthotic devices according to one or more methods disclosed herein. FIG. 26 shows an embodiment of a first (or "waves") personalized material portion 710, an embodiment of a second (or "bio-mechanical design") personalized material portion 712, an embodiment of a third personalized material portion 714, and an embodiment of a fourth personalized material portion 716.

In further embodiments, a method of personalizing an orthotic or a prosthetic device may include sublimation of custom transfer paper tattoo art prints, which also may be termed a custom cosmetic treatment. In some embodiments, such a sublimation process may include applying transfer paper art to an orthotic or a prosthetic device, thereby allowing personalization and printing allowing the wearer to make a personal choice or self expression with tattoo art by furnishing a personal digital camera image, clip art, three-dimensional (3D) high graphic images, or other suitable art. In some embodiments, a user may make a selection from a library of pre-selected designs.

In further embodiments, a print is pre-ordered by a wearer, prior to the fabrication process, and is applied by a third party (e.g. orthotist, prosthetist, technician, etc.). The custom transfer art print can be installed onto PolyPro, CoPoly, or other plastic types. The transfer paper print may be laid on top of the plastic substrate while the plastic is still in the oven, and may become an integral part and fused to the plastic. In at least some embodiments, the installation of the transfer paper is done prior to pulling the plastic over the cast, mold or CNC carved foam and vacuum pulled during the clinical fabrication. Such a method can be used at an assembly line in other non-custom manufactured plastic orthotics devices, including, but not limited to: Cranial Helmets, Lumbar Jackets, Arm Braces, Prosthetic limbs, both upper and lower extremity fabricated limbs, Knee Ankle Foot Orthosis (KAFO), and/or Ankle Foot Orthosis (AFO). Such processes may be available directly to the consumer, or through a prosthetist who can preorder for a patient by special order through several "OandP" (Orthotic and Prosthetic) supply distribution centers.

In still further embodiments, systems and methods for personalizing prosthetic and orthotic may include choosing a wearer choosing a preselected art design or providing an image of their choice. The image may be custom modified by a graphic designer (e.g. by means of utilizing Photoshop™) to enlarge, and/or collage the image to a specific size. A proof may be provided (e.g. email) to a customer for approval prior to application. After approval, the image is printed on a transfer paper, which may be similar or the same as conventional transfer paper. In at least some embodiments, the prints may be a high quality, sublimation full color image. The print may then be shipped in a mailer tube package to the wearer, and installed by the wearer or a suitable third party (e.g. prosthetist, orthotist, OandP technician, etc.).

In still further embodiments, a method in accordance with the teachings of the present disclosure may include sublimination of custom fabric tattoo art prints on OandP devices and can be applied onto upper and lower extremity prosthetic (prostheses) limbs and/or many suitable orthotic braces. Again, such methods allow personalization and printing, allowing the wearer to make a personal choice or self expression with tattoo art by furnishing a personal digital camera image, clip art, 3D high graphic images or they make a selection from a library pre-selected designs. The custom fabric prints may be installed by third-party technicians and prosthetist and orthotist, and may be laminated with 100% acrylic resin.

In at least some embodiments, such custom fabric prints can be applied over several substrates of common materials used to fabricate prosthetic limbs and orthotic braces, including, for example, compositions of (or including) carbon braid, fiberglass, or nylon substrates. Similarly, in at least some embodiments, such custom fabric prints may be applied to a variety of devices, including but not limited to, orthotic braces clinical custom fabricated and other pre-manufactured braces. Again, in some embodiments, such processes may be available to the consumer, or through a prosthetist who can preorder for a patient by special order through several OandP supply distribution centers (e.g. SPS and Cascade), and may also be available for pre-manufactured plastic orthotic companies. Devices that this method can applied to include, for example, Cranial Helmets, Arm Braces, Prosthetic limbs, both upper and lower extremity fabricated limbs, Knee Ankle Foot Orthosis (KAFO), and Ankle Foot Orthosis (AFO).

Methods that include sublimination of custom fabric tattoo art prints can also be supplied to OandP manufacturers who may fuse such a fabric over a silicone liner during a specialty manufacturing process. The silicone liner may then be used by the wearer or amputee donned and applied over the residual limb. Such a method may also be supplied to OandP manufacturers, who may fuse a fabric over a silicone suspension sleeve during the specialty manufacturing process. The silicone suspension sleeves used by the wearer or amputee support and attach the prosthetic limb to the residual limb.

In a further embodiment, a method may include: (a) choosing an image for application onto a prosthetic or orthotic device (e.g. prosthetist, orthotist or wearer of device chooses a preselected art design or can provide an image of their choice); (b) custom modifying the image (e.g. a graphic designer modifying the image by means of utilizing Photoshop to enlarge, collage the image to a specific size); (c) determining a size of the image to be applied based on dimensions of the device (e.g. height and width of image to be applied based on the height and circumference of the device); (d) providing the final image to the customer for approval (e.g. via email); and (e) after approval, the print is printed on a suitable fabric (e.g. 97% cotton with 3% spandex, cotton/polyester blend with a 3% spandex, etc.). In at least some embodiments, the material may be permeable to allow for the 100% acrylic resin to fuse and saturate through the fabric when laminated over typical substrates. In at least some embodiments, the print may be a high quality, sublimation full color image. One or more additional prints may be supplied on each order that can be used on their next fabricated assistive device. The method may further include (e) providing the final print to the customer (e.g. the print may be shipped in a mailer package to the wearer), and (f) installing the print on an orthotic or prosthetic device (e.g. by third party prosthetist, orthotist, OandP technician, etc. or by the wearer).

In further embodiments in accordance with the teachings of the present disclosure, methods and apparatus for personalizing an orthotic or prosthetic device may include disposing a Global Positioning System (GPS) locator in or on the device. Such a GPS locator may advantageously assist in locating a prosthetic limb device in the event it is stolen or lost. In some embodiments, a GPS transmitter chip may be installed by the prosthetic limb manufacturer during the assembly. Alternately, a GPS transmitter chip may be available as an after-market add on that can be installed to existing prosthetic limbs (e.g. by the wearer or by a prosthetist or OandP technician) at the clinical level.

In some embodiments, a transmitter chip is placed onto the prosthetic device and attached with epoxy or other bonding agent or method to the prosthetic limb substrate. Each transmitter may have a serial number and may be monitorable by a third party. In some embodiments, for example, a subscription with a monitoring company (e.g. LoJack) may be activated by the wearer, or by a health insurance company or the entity or provider who purchases a GPS locator for prosthetic limbs security system.

In further embodiments in accordance with the teachings of the present disclosure, methods and apparatus for personalizing an orthotic or prosthetic device may include providing one or more lights on the device. For example, in some embodiments, a light assembly may have a light emitting portion (e.g. LED or the like), a protective cover (e.g. lens), a power unit (e.g. battery), and may be attached to the orthotic or prosthetic device using a bonding agent (e.g. epoxy, peel and stick contact paper, etc.). In at least some embodiments, the light may be a blinking on and off alternating flashing light which is activated only by motion.

Figure 27:
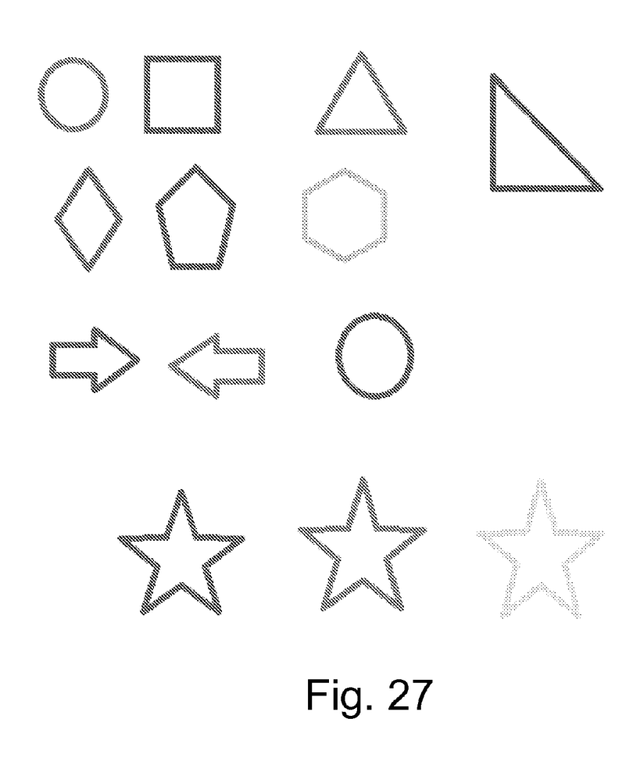

FIG. 27 shows views of various exemplary lights and/or designs for application to prosthetic or orthotic devices in accordance with further embodiments of the present disclosure. Lighting devices in accordance with the teachings of the present disclosure may vary in size depending on the shape of object (e.g. average size 1 cm, 1.5 cm, or ½"-¾", etc.). Lights may be applied in various quantities and mixed or single shapes.

It will be appreciated that the detailed descriptions of the above embodiments are not exhaustive descriptions of all embodiments contemplated by the inventor to be within the scope of the invention. Indeed, it will be recognized that certain aspects or elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the present disclosure. Accordingly, the scope of the invention should be determined from the following claims.

What is claimed is:

1. A method of personalizing a device configured to be worn by a wearer, comprising:
providing the device configured to be worn by the wearer, the device being at least one of a prosthetic device or an orthotic device;
receiving input from the wearer regarding a personalizing attachment the wearer selects to be applied to at least a portion of an exterior surface of the device; preparing the at least a portion of the exterior surface of the device configured to be worn by the wearer, wherein preparing the at least a portion of the exterior surface of the device comprises:
cleaning the at least a portion of the exterior surface of the device;
dry-sanding the at least a portion of the exterior surface of the device;
coating the at least a portion of the exterior surface of the device with a primer;
wet-sanding the at least a portion of the exterior surface of the device;
base-coating the at least a portion of the exterior surface of the device with a basecoat;
applying one or more substantially-clear coatings to the at least a portion of the exterior surface of the device;
applying one or more intermediate coatings to the at least a portion of the exterior surface of the device; and
wet-sanding the one or more intermediate coatings; and
applying an electronic tracking device that emits one or more electromagnetic signals to the at least a portion of the exterior surface of the device configured to be worn by the wearer.

2. A method of personalizing a device configured to be worn by a wearer, the method comprising:
providing the device configured to be worn by the wearer, the device being at least one of a prosthetic device or an orthotic device;
receiving an indication of a selection of a personalizing artwork to be applied to at least a portion of an exterior surface of the device configured to be worn by the wearer;
preparing the at least a portion of the exterior surface of the device configured to be worn by the wearer, wherein preparing the at least a portion of the exterior surface of the device comprises:
cleaning the at least a portion of the exterior surface of the device;
dry-sanding the at least a portion of the exterior surface of the device;
coating the at least a portion of the exterior surface of the device with a primer;
wet-sanding the at least a portion of the exterior surface of the device;

base-coating the at least a portion of the exterior surface of the device with a basecoat;
applying one or more substantially-clear coatings to the at least a portion of the exterior surface of the device;
applying one or more intermediate coatings to the at least a portion of the exterior surface of the device; and
wet-sanding the one or more intermediate coatings;
applying the personalizing artwork to the at least a portion of the exterior surface of the device configured to be worn by the wearer, including at least applying at least one of a clip art or a graphic provided by the wearer to the at least a portion of the exterior surface of the device; and
applying one or more substantially-clear top coatings over the wearer-selected artwork.

3. The method of claim 2, wherein cleaning the at least a portion of the exterior surface of the device comprises:
cleaning the at least a portion of the exterior surface of the device using at least one of an acryi-clean product or a rubbing alcohol.

4. The method of claim 2, wherein dry-sanding the at least a portion of the exterior surface of the device comprises:
dry-sanding a braided carbon substrate using at least one of a dry sandpaper or a non-sandpaper abrasive product.

5. The method of claim 2, wherein applying the wearer-selected artwork to the at least a portion of the exterior surface of the device configured to be worn by the wearer comprises:
securing a three-dimensional (3d) piece of artwork onto the at least a portion of the exterior surface of the device.

6. The method of claim 2, wherein applying the personalizing artwork to the at least a portion of the exterior surface of the device configured to be worn by the wearer comprises:
applying a photo provided by the wearer to the at least a portion of the exterior surface of the device.

7. The method of claim 2, wherein providing a device configured to be worn by a wearer, the device being at least one of a prosthetic device or an orthotic device comprises:
providing a device configured to be worn at least one of on or proximate to an outer surface of at least one of a limb or a torso of a wearer, the device being at least one of a prosthetic device or an orthotic device.

8. The method of claim 2, wherein applying the personalizing artwork to the at least a portion of the exterior surface of the device configured to be worn by the wearer comprises:
creating a collage of one or more portions of artwork provided by the wearer; and
applying the collage of one or more portions of artwork to the at least a portion of the exterior surface of the device.

9. The method of claim 2, wherein applying the personalizing artwork to the at least a portion of the exterior surface of the device configured to be worn by the wearer comprises:
sublimation printing of at least one portion of artwork to the at least a portion of the exterior surface of the device.

10. The method of claim 9, wherein sublimation printing of at least one portion of artwork to the at least a portion of the exterior surface of the device comprises:
sublimation printing of at least one of an image on fabric or an image on paper to the at least a portion of the exterior surface of the device.

11. The method of claim 2, wherein applying the personalizing artwork to the at least a portion of the exterior surface of the device configured to be worn by the wearer comprises:
applying a personalizing artwork using a dye to the at least a portion of the exterior surface of the device.

12. The method of claim 2, wherein applying the personalizing artwork to the at least a portion of the exterior surface of the device configured to be worn by the wearer comprises:
applying a light to the at least a portion of the exterior surface of the device.

13. The method of claim 2, wherein applying the personalizing artwork to the at least a portion of the exterior surface of the device configured to be worn by the wearer comprises:
applying a motion-activated light to the at least a portion of the exterior surface of the device.

14. A method of personalizing a device configured to be worn by a wearer, the method comprising:
providing the device configured to be worn by the wearer, the device being at least one of a prosthetic device or an orthotic device;
receiving an indication of a selection of a personalizing artwork the wearer selects to be applied to at least a portion of an exterior surface of the device configured to be worn by the wearer;
preparing the at least a portion of the exterior surface of the device configured to be worn by the wearer, wherein preparing the at least a portion of the exterior surface of the device comprises:
cleaning the at least a portion of the exterior surface of the device;
dry-sanding the at least a portion of the exterior surface of the device;
coating the at least a portion of the exterior surface of the device with a primer;
wet-sanding the at least a portion of the exterior surface of the device;
base-coating the at least a portion of the exterior surface of the device with a basecoat;
applying one or more substantially-clear coatings to the at least a portion of the exterior surface of the device;
applying one or more intermediate coatings to the at least a portion of the exterior surface of the device; and
wet-sanding the one or more intermediate coatings; and
facilitating the application of the personalizing artwork to the at least a portion of the exterior surface of the device configured to be worn by the wearer.

15. The method of claim 14, wherein facilitating the application of the personalizing artwork to the at least a portion of the exterior surface of the device configured to be worn by the wearer comprises:
creating a portion of material having the personalizing artwork; and
providing the portion of material having the personalizing artwork for application onto the at least a portion of the exterior surface of the device configured to be worn by the wearer.

16. The method of claim 15, wherein providing the portion of material having the personalizing artwork for application onto the at least a portion of the exterior surface of the device comprises:
providing the portion of material for application when the at least a portion of the exterior surface of the device is being fabricated.

17. The method of claim 14, wherein facilitating the application of the personalizing artwork to the at least a portion of the exterior surface of the device configured to be worn by the wearer comprises:
applying a photo provided by the wearer to the at least a portion of the exterior surface of the device.

18. The method of claim 14, wherein facilitating the application of the personalizing artwork to the portion of the device configured to be worn by the wearer comprises:
applying a three-dimensional piece of artwork to the at least a portion of the exterior surface of the device.

19. The method of claim 14, wherein facilitating the application of the personalizing artwork to the at least a portion of the exterior surface of the device configured to be worn by the wearer comprises:

applying a light emitting device to the at least a portion of the exterior surface of the device.

* * * * *